United States Patent [19]

Brantigan

[11] Patent Number: 4,834,757
[45] Date of Patent: May 30, 1989

[54] PROSTHETIC IMPLANT

[76] Inventor: John W. Brantigan, 2108 Bramblewood La., Fremont, Nebr. 68025

[21] Appl. No.: 173,928

[22] Filed: Mar. 28, 1988

Related U.S. Application Data

[63] Continuation-in-part of Ser. No. 5,785, Jan. 22, 1987, Pat. No. 4,743,256, which is a continuation of Ser. No. 784,112, Oct. 4, 1985, abandoned, and a continuation-in-part of Ser. No. 95,461, Sep. 11, 1987.

[51] Int. Cl.$^4$ .............................................. A61F 2/44
[52] U.S. Cl. ...................................... 623/17; 623/16; 128/92 YG; 128/92 YM
[58] Field of Search ...................... 623/17, 16, 18, 21, 623/22, 23, 66; 128/92 YG, 92 YM, 92 YJ, 92 W, 305

[56] References Cited

U.S. PATENT DOCUMENTS

| | | |
|---|---|---|
| 2,677,369 | 5/1954 | Knowles . |
| 3,228,393 | 1/1966 | Michele ............................ 128/92 YJ |
| 3,426,364 | 2/1969 | Lumb . |
| 3,848,601 | 11/1974 | Ma et al. ............................ 128/305 |
| 3,855,638 | 12/1974 | Pilliar . |
| 3,867,728 | 2/1975 | Stubstad et al. . |
| 3,871,031 | 3/1975 | Boutin ............................ 623/18 X |
| 3,893,196 | 7/1975 | Hochman ............................ 623/18 |
| 4,206,516 | 6/1980 | Pilliar . |
| 4,309,777 | 1/1982 | Patil . |
| 4,349,921 | 9/1982 | Kuntz ............................ 623/17 |
| 4,550,448 | 11/1985 | Kenna . |
| 4,553,273 | 11/1985 | Wu . |
| 4,559,086 | 7/1986 | Doty . |
| 4,743,258 | 5/1988 | Ikada et al. ...................... 623/66 X |

OTHER PUBLICATIONS

PoroCoat—A Technical Review of Porous-Coated Implants for Biological Fixation-DePuy.
Article "Anterior Discectomy and Interbody Fusion for Lumbar Disc Herniation"—Inoue, M.D. et al No. 183, Mar. 1984.
Article—"Clinical Orthopaedics and Related Research" No. 193 Mar. 1985.

Primary Examiner—Richard J. Apley
Assistant Examiner—Alan W. Cannon
Attorney, Agent, or Firm—Hill, Van Santen, Steadman & Simpson

[57] ABSTRACT

Gauge blocks or plugs and permanent implant plugs are provided for surgical procedures to support and fuse together adjacent vertebrae in a vertebral column. The plugs are rectangular with tapered front ends and tool receiving rear ends. The gauge blocks are smooth faced for removal but the implant plugs have roughened surfaces to grip the vertebrae and provide channels for bone ingrowth. The plugs have recesses in the form of through slots to be packed with bone graft material. In the surgical procedure, undamaged annulus fibrosus disc tissue connecting the adjacent vertebrae is preserved and a pair of side-by-side roughened implant plugs are forced into side-by-side transverse channels in the adjoining vertebrae to stretch the remaining annulus disc tissue and form struts supporting the vertebrae. The plugs are bottomed in the channels on cortex bone and bone ingrowth is facilitated to fuse the plugs to the vertebrae.

11 Claims, 2 Drawing Sheets

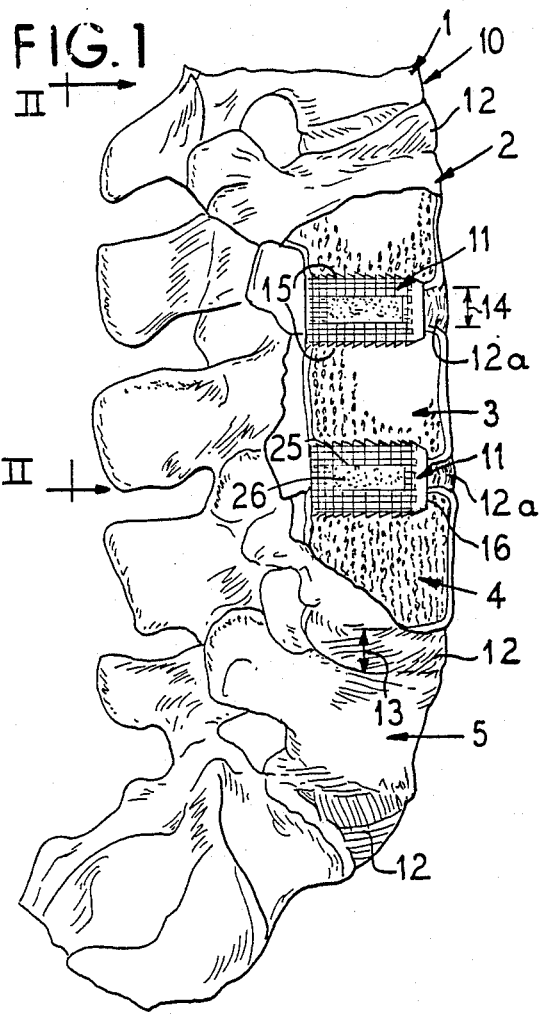
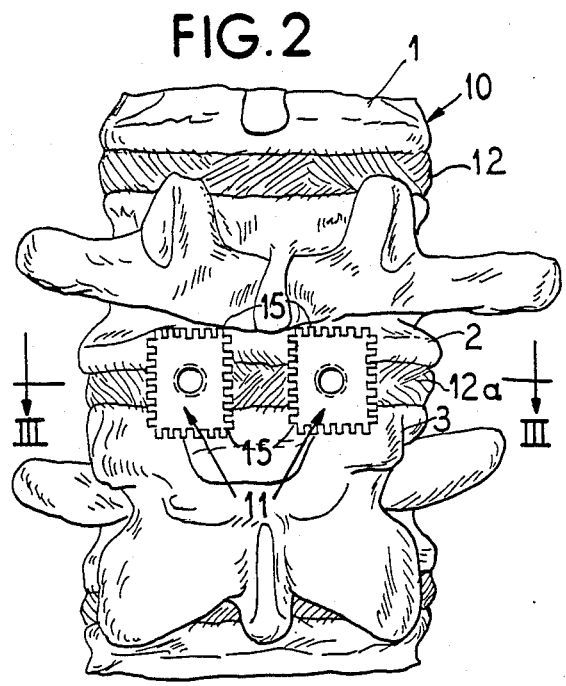
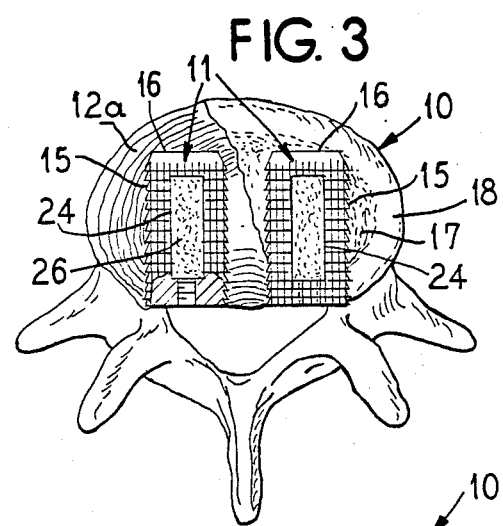
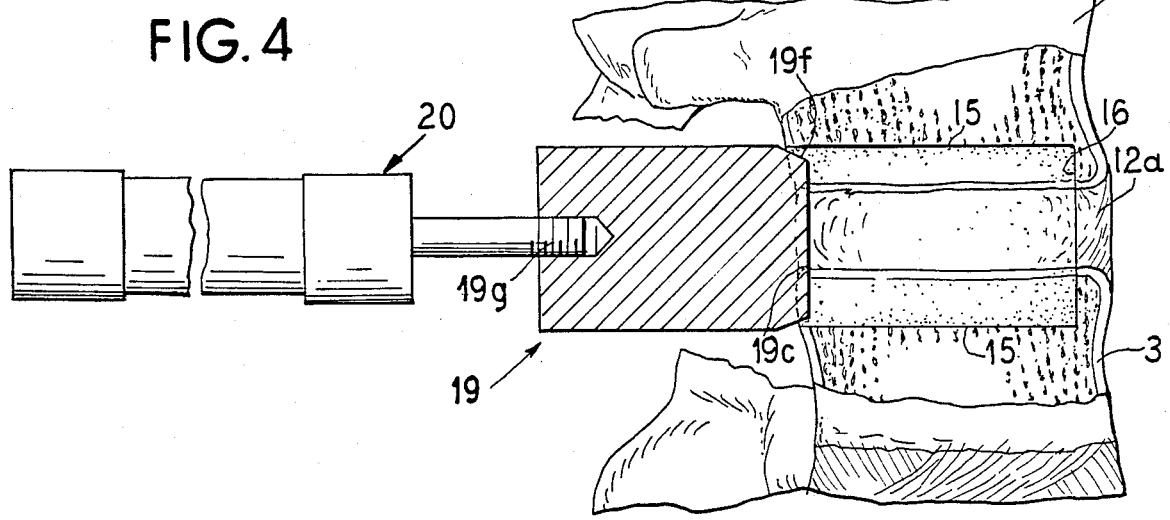

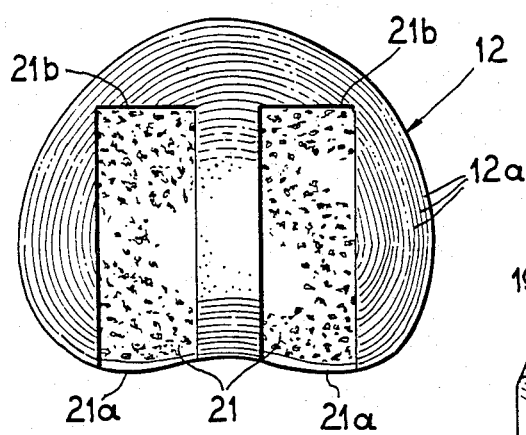
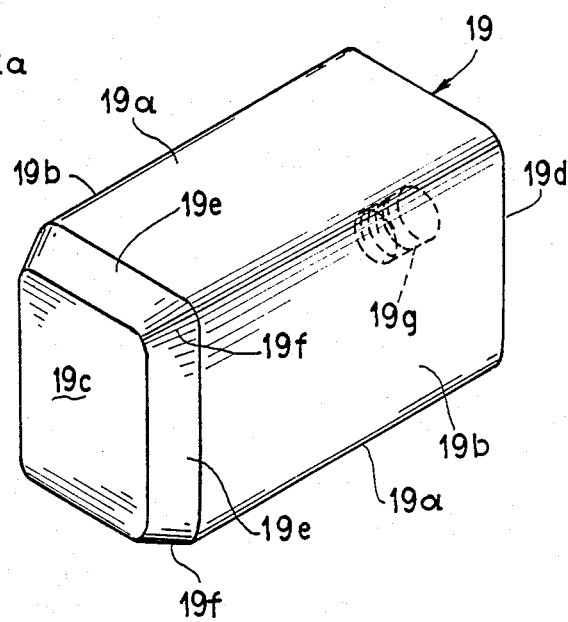
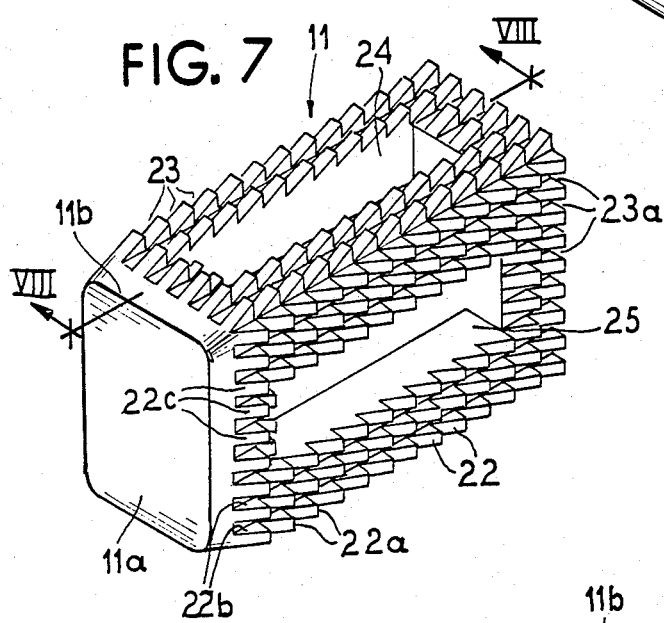
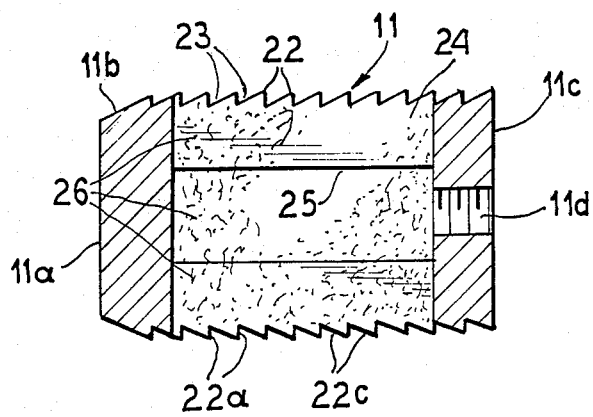

PROSTHETIC IMPLANT

RELATED APPLICATIONS

This application is a continuation-in-part of Ser. No. 005,785, filed Jan. 22, 1987, now U.S. Pat. No. 4,743,256, which is a continuation of Ser. No. 784,112, filed Oct. 4, 1985, abandoned, and is also a continuation-in-part of Ser. No. 095,461, filed Sept. 11, 1987

BACKGROUND OF THE INVENTION

Field of the Invention

This invention relates to the art of prosthetic devices and methods for implanting the devices between adjacent vertebrae to treat or prevent back pain in patients with ruptured or degenerated intervertebral discs. Specifically this invention deals with improvements in prosthetic strut forming plugs or blocks with roughened surfaces facilitating bone ingrowth from adjoining vertebrae wherein the blocks are shaped to fit in rectangular slots cut in the vertebrae, have heights which will stretch the remaining elastic annulus tissues of damaged discs between the adjoining vertebrae and have slots extending vertically, transversely or both vertically and transversely through the plugs to be packed with bone grafts to expedite the bone ingrowth.

More specifically the plugs or blocks fitting the rectangular slots in the adjoining vertebrae have tapered leading ends facilitating insertion into the slots between the vertebrae to stretch remaining disc tissue connecting the vertebrae and tool receiving trailing ends for forcing the plugs into position. A still further specific feature of the invention is the provision of plugs which are radiolucent for improved X-ray visualization of the bone healing post-operatively.

As pointed out in my aforesaid parent U.S. Pat. No. 4,743,256 its continuation-in-part application Ser. No. 095,461, the leading cause of low back pain arises from rupture or degeneration of lumbar intervertebral discs. Pain in the lower extremities of the back (sciatica) is caused by the compression of spinal nerve roots by damaged discs between the vertebrae and low back pain is caused by collapse of the disc and the adverse effects of bearing the majority of the body weight through a damaged unstable vertebrae joint. Surgical treatments for relief of the sciatic pain and lower back pain generally include the following:

(1) EXCISION OF THE RUPTURED SOFT DISC

This procedure removes the portion of the disc compressing the spinal nerve and is generally successful in relieving the sciatic leg pain but in more than half of the cases, there is a recurrence of back pain. Over a period of time the disc gradually loses height due to the rupture and this loss of height causes the posterior facet joints of the vertebrae to fit incorrectly resulting in arthritic change in all elements of the spinal segment. Recurrent nerve root compression due to bony encroachment (spinal stenosis) also develops. The continuing and recurring back pain from this source has created a leading source of pain and disability.

(2) DISC EXCISION WITH POSTERIOR FUSION

Traditional posterior fusion, creating bone growth between the bony laminae, or postero-lateral fusion between the transverse processes prevents motion between the adjacent vertebrae but does not alter the fact that approximately 90% of the body weight must be transmitted through degenerated discs causing pain. Further, posterior fusion tends to cause bony overgrowth leading to nerve root compression by spinal stenosis.

(3) DISC EXCISION WITH ANTERIOR INTERBODY FUSION

Interbody fusion techniques, in which the soft disc is completely excised and replaced with either the patient's own bone (autologous bone) or with transplant banked bone (homologous bone) are generally successful if solid fusion can be obtained between adjacent vertebrae bodies. Unfortunately, the success rate has only been about 50%.

(4) DISC EXCISION WITH POSTERIOR LUMBAR INTERVERTEBRAL FUSION (PLIF)

This procedure reconstructs the normal anatomic relationships between the bony and the neural structures and has many advantages. Weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

However, this PLIF procedure has several serious disadvantages in that it is technically very difficult, and, therefore, not as successful or widely used as it might be. It entails large amounts of blood loss in a small deep hole causing physiological stress to the patient and psychological distress to the surgeon. Further, the use of autologous bone graft from the patient's own iliac crests extends the operation and creates a second painful operative site. Because it is difficult to obtain a large enough quantity of autogenous bone with sufficient strength, homologous bank bone is generally used.

Interbody bone grafting involves the problems of strength and that of bone incorporation. Strong cortex bone (the outer layer) is required as a strut in the interbody position to prevent collapse of the disc space while healing occurs. The surgeon has the unfortunate requirement of having to fashion the required struts with handheld tools during the operation and these cortex bone struts are not wide enough for optimum load bearing and they anchor themselves by healing process that occurs very slowly over a matter of years. Further, soft cancellous bone, which heals more reliably over a matter of 12 to 18 months, is also required for a traditional interbody fusion.

It is well understood in orthopaedic surgery, that grafted bone heals by a process called "creeping substitution" in which blood capillaries first grow into the grafted bone, the grafted bone is reabsorbed, and then new bone cells are laid down along the bony matrix of the graft. During the time that the structural bone grafts struts are being reabsorbed, motion must still be prevented in the involved segments and although a brace or cast is often used, the entire process has proven less reliable than desired. Homologous bank bone, being more "foreign", requires a much longer time to grow together and has a higher failure rate estimated at three times the failure as with the patient's own bone. In effect, neither source of bone is optimum for the fusion procedure.

My prior aforesaid U.S. Pat. No. 4,743,256 discloses an improved surgical procedure for eliminating spinal back pain caused by ruptured or degenerated vertebral discs by spanning the disc space between adjacent vertebrae with rigid implants having surfaces facilitating bone ingrowth and bottomed on prepared sites of the vertebrae to integrate the implant with the vertebrae and to provide a permanent weight supporting strut maintaining the disc space.

My prior aforesaid patent application Ser. No. 095,461, filed Sept. 11, 1987, discloses a further improved surgical procedure by providing the rigid implants or blocks with tool receiving end faces facilitating their insertion onto the prepared sites and having geometric patterns of roughened surfaces on the peripheries of the implants enhancing the bone growth. Novel tools are releasably attached to the end faces of these implants.

The present invention now still further improves this art by providing a group of smooth faced trial or gauge blocks or plugs of different heights and widths for temporary insertion in the rectangular grooves or slots cut into the adjacent vertebrae to locate a plug that will tightly fit the slots and stretch the disc tissue a desired amount. This procedure permits the surgeon to select a permanent implant plug with a rough surface of a slightly larger size that can be force fitted into permanent position to further stretch the annulus tissue fibers of the disc still connecting the vertebrae placing them under tension thus facilitating their growth and also causing the vertebrae to tightly grip the plug. Further, the permanent impact plugs are provided with beveled or taped leading ends to spread the vertebrae apart and facilitate insertion into the rectangular channels or slots. Still further, the plugs may have vertical, horizontal, or both horizontal and vertical intersecting slots therethrough packed with bone grafts to expedite bone ingrowth. Also, the plugs can be made of radiolucent material to facilitate x-ray inspection of the bone growth.

SUMMARY OF THE INVENTION

The present invention now provides vertebral prosthesis implant plugs or blocks fitting rectangular transverse or perpendicular channels or grooves cut in the adjoining faces of vertebral bodies having heights that will stretch the remaining annulus tissue of the discs therebetween still connecting the vertebrae. According to this invention, parallelepiped blocks or plugs are provided to fit these transverse rectangular channels or slots and have beveled or tapered leading ends easily inserted into the open ends of the transverse slots to spread the vertebrae apart so that the top and bottom faces of each block or plug is tightly bottomed in the slot with the stretched disc tissues causing the vertebrae to grip the plugs. These plugs are inserted laterally or transversely of the vertebral column into the slots while mounted on the end of an insertion tool, have roughened surfaces to facilitate the bone ingrowth and also have vertical or horizontal slots therethrough or intersecting vertical and horizontal slots packed with bone graft material, such as strips of bone excised from the iliac crest of the pelvis. This implant material provides a block of living bone that grows all around and though the implant plug into the bone of the vertebrae.

Also, according to this invention, the blocks or plugs instead of being made of an inert metal, such as stainless steel, titanium, cobalt-chromium-molybdenum alloys and the like, can be made of a radiolucent material, such as a plastic of the nylon, polycarbonate, polypropylene, polyacetal, polyethylene, and polysulfone type, preferably filled with glass or carbon fibers. These plastics can be injection molded, are light in weight, have great load carrying strength and provide improved x-ray visualisation of bone healing. Fiber reinforced plastics composed of such materials filled with glass or carbon fibers are also desirable. Suitable carbon fiber composites are supplied under the tradename "VICTREX P.E.S." which is polyether sulfone filled with carbon fibers. Suitable grades are "4101 G.L.-30" which is a 30 percent fiber glass filled and "450 C.A.-30" which is a 30 percent carbon fiber filled. These materials are supplied from ICI Industries of Wilmington, Del. Carbon-carbon fiber plastics of the type sold by Fiber-Rite Corporation of Winona, Minn., are useful.

The roughened surfaces of the permanent implant plugs are non-yielding and have configurations to best grip the channels of the vertebral body and to permit bone ingrowth therebetween.

Preferred embodiments of the invention are illustrated in the annexed drawings in which:

FIG. 1 is a side-elevational view of the lower portion of a human vertebrae column with parts broken away and shown in section to illustrate flat-sided rectangular prosthetic implant plugs or blocks of this invention inserted in rectangular grooves or channels in the opposed faces of adjacent vertebrae to support the vertebrae in place of the human disc therebetween which has been partially excised to remove damaged and herniated tissue.

FIG. 2 is a posterior elevational view of a portion of FIG. 1 taken along the line II—II of FIG. 1.

FIG. 3 is a transverse sectional view, with parts in elevation and broken away in section, along the line III—III of FIG. 2.

FIG. 4 is an enlarged fragmentary side-elevational view with parts broken away and shown in vertical section illustrating the manner in which a trial or gauge plug or block of this invention is inserted in position in the transverse rectangular slots of adjoining vertebrae to stretch the remaining interposed disc tissue connected to these vertebrae and to gauge the sites for receiving a proper sized permanent implant.

FIG. 5 is a plan view of a vertebrae disc with the interior pulp removed and with disc tissue partially excised to provide gaps or slots aligned with channels cut in the vertebrae to receive the plugs therethrough.

FIG. 6 is a perspective view of a smooth faced trial or gauge plug or block for use as shown in FIG. 4.

FIG. 7 is a perspective view of a preferred form of permanent implant plug or block of this invention.

FIG. 8 is a longitudinal vertical sectional view of the plug of FIG. 7 taken along the line VIII—VIII of FIG. 7.

As Shown on the Drawings:

In FIGS. 1–3, the reference numeral 10 illustrates generally the lower portion of a human vertebral column with adjacent vertebrae supported on prosthetic implant blocks or plugs 11 of this invention.

FIG. 4 shows the manner in which adjacent vertebrae are spread apart to stretch intervening disc tissue as a gauge or trial block of this invention is inserted laterally into transverse rectangular slots of adjoining vertebrae.

In FIG. 1, the vertebral column 10 shows the five lower vertebrae Nos. 1–5. Adjacent vertebrae Nos. 2 and 3 and adjacent vertebrae Nos. 3 and 4 are separated by and supported on the prosthetic implant blocks or plugs 11 of this invention. Vertebrae Nos. 1 and 2 and vertebrae Nos. 4 and 5 are illustrated as supported on and separated by healthy or undamaged human discs 12 maintaining a disc space 13 between the adjoining vertebrae.

Damaged portions of the natural human discs 12 have been excised from the vertebrae Nos. 2 and 3 and Nos. 3 and 4 with the disc spaces 14 being maintained by the implant blocks or plugs 11. It is preferred to retain as much as possible of the healthy annulus tissue of the discs 12 between the vertebrae so that the remaining disc tissue 12a will at least partially surround the implants and will be held under tension by these implants. However, some of the remaining disc tissue may have to be excised to open up spaces for the implant plugs 11.

The opposed faces of adjoining vertebrae with damaged discs therebetween have aligned flat-sided rectangular channels or grooves 15 cut therein transversely of the axis of column 10 to first snugly receive test blocks or plugs of this invention for determining the proper sizes for the permanent implants 11. These transverse channels 15 are sufficiently wide and deep to span the central soft cancellous bone and include the hard cortex bone of the adjacent vertebrae. The undamaged human disc tissue 12a remaining between the vertebrae is also cut or trimmed to receive the implants 11 so that as much healthy annulus fibrous tissue as is available will surround the implants.

The preferred flat-sided rectangular channels 15 have blind ends 16 to be abutted by the implants 11.

As shown in FIGS. 2 and 3, the implants 11 are in the form of a pair of side-by-side rectangular (specifically parallelepiped) plugs inserted endwise into the transverse channels 15. These channels have flat bottoms and sidewalls to snugly embrace the top and bottom ends and side faces of the rectangular plugs. The soft cancellous bone of the vertebrae is illustrated at 17 in FIG. 3 and is surrounded by the hard cortex bone 18. The channels 15 include portions of this hard cortex bone so that the implants 11 span the softer cancellous bone and rest on the hard cortex bone 18.

The channels 15 can be formed by a mortise cutting chisel tool and in the event disc tissue 12a blocks the paths for the plugs 11, tissue can be trimmed or spread apart to open up the paths.

The implant plugs of blocks 11, as shown in FIGS. 7 and 8, are rigid, inert, solid, parallelepiped, higher than wide and longer than high. They are used in cooperation with trial or gauge blocks, such as 19, shown in FIG. 6. These blocks 19 have flat, smooth sides and ends with flat top and bottoms 19a, flat sides 19b, a flat front end wall 19c, a and a flat back end wall 19d. The front wall 19c is beveled to a reduced rectangular nose surrounded by flat-sided tapered walls 19e with rounded corners 19f.

The back end wall 19d has an internally threaded blind axial hole 19g at the center of the wall.

The gauge blocks 19, in typical surgical operations, will have a length of about 25 mm, a width of about 11 mm and will vary in height from, say, 13 to 17 mm, although it should be understood that these parameters may vary greatly and may depend on the size of the spinal column of the recipient. The tapers 19e are preferably about 30 degrees. The rounded corners 19f of the bevels eliminate sharp corners between the top, bottom and sides of the beveled faces.

As shown in FIG. 4, a trial or gauge block 19 is selected for force-fitting into the channels 15 while mounted on a tool 20 threaded into the hole 19g. The beveled front end 19c of the block will pass through any portion of the disc tissue 12a covering the entrance mouths of the channels 15 by either cutting holes through the remaining tissue or by spreading apart the fibers of the disc to accept the gauge blocks 19.

As shown in FIG. 5, the remaining healthy disc tissue 12a of a disc 12 between the channel cut vertebrae is trimmed to open up slots 21 permitting access of the gauge blocks 19 to the channels 15. These slots register with the channels 15 and can have open front ends 21a and blind back ends 21b. It is preferred to remove the nucleus pulposus from the damaged disc 12 leaving an annulus of fibrous tissue connecting the adjoining vertebrae and surrounding the inserted blocks.

A proper fitting gauge block 19 is selected by trial and error insertions into the channel cut vertebrae. These blocks are smooth faced and can be removed even when tightly fitted in the channels 15.

As shown in FIG. 4, a gauge block 19, threaded on the end of an insertion tool 20 is selected to have a height greater than the free span between the bottoms of opposed channels 15. Then, when this block is pushed through the open ends of the aligned channels 15, the beveled nose 19c will engage the bottoms of these channels forcing them apart as the block is pushed into the channels thereby stretching any disc tissue 12a still connecting the vertebrae. The block is pushed against the blind ends 16 of the channels and the tension on the disc fibers is determined. When a block 19 of sufficient size to properly load the disc tissue and to fit snugly in the channel, is located, a permanent implant plug 11 of a size just slightly greater than the gauge block is selected. Such a permanent plug is then threaded on the end of a tool 20, the gauge block 19 is withdrawn, and the permanent implant 11 on the tool is forced into a position in the channels 15.

A preferred permanent implant block or plug 11 is illustrated in FIGS. 7 and 8. This plug has about the same flat side dimensions as the selected gauge block, but has projected from these flat top, bottom and sidewalls, a pattern of raised annular nubs 22 providing a roughened surface, biting into and gripping the bottoms and sidewalls of the rectangular channels 15. These nubs are separated by annular grooves 23 and longitudinal channels 23a so that each nub 22 will have a flat vertical back wall 22a, a pair of flat vertical sidewalls 22b and an inclined front face 22c.

The plug 11 has the same reduced nose 11a surrounded by the same beveled sidewalls 11b as the nose 19c and beveled sidewall 19e of the gauge block 19. In addition a vertical back wall 11c is the same as the back wall 19d and contains the same internally threaded hole 11d as the back walls 19d and 19g of the gauge block 19.

Further, the implant plug 11 has a vertical slot 24 therethrough connecting the tops and bottoms of the plug. This vertical slot 24 is rectangular, has a width about ⅓ the width of the block and a length extending close to the front and rear ends of the plug.

This slot 24 is intersected centrally by a horizontal through slot 25. It will be understood that, alternately, the block 11 may have only a single horizontal or vertical slot.

The slots 24 and 25 provide cavities in the block or plug 11 which are filled with strips of bone implant 26 preferably harvested from the pelvis bone of the recipient. This bone material housed in the implant plugs 11 will soon grow out of the grooves or channels 24 and 25 into the radial and longitudinally channels between the nubs 22 surrounding the plug 11 and will then grow into the bone tissue of the adjoining vertebrae.

When the implant plug is pushed into its seated position between the vertebrae, the inclined front faces of the nubs 22 will accommodate the forward moving of the plug to the blind ends 16 of the channels 15, but the sharp apexes of the nubs will prevent retraction of the plugs since they will bite into the vertebrae bone. Therefore, once the plugs are seated in proper position, they will not shift from this position.

It is preferred that the heights of the plugs 11 will be sufficient to maintain a tension load of about 20 to 30 pounds on the disc tissue. Such a tension load not only pulls the vertebrae tightly against the plugs, but also accelerates bone ingrowth.

The preferred prosthesis plugs or blocks 11 of this invention not only facilitate and simplify the surgical procedure but also accelerate interbody fusion of the vertebrae with the plug. The roughened surfaces provided by the nubs thus serve a multiple purpose of anchoring into the vertebrae, and providing channels for bone ingrowth.

From the above descriptions it will therefore be understood that this invention provides important advantages in the surgical procedures for preventing back pain in patients with damaged intervertebral discs.

I claim as my invention:

1. A surgical prosthetic device adapted for fusing together adjoining vertebrae bodies connected by tissue of a damaged collapsed disc and having spaced opposed faces on opposite sides of the disc space therebetween with transverse channels in said faces including hard peripheral cortex bone surrounding central cancellous bone which comprises a rigid inert parallelpiped plug sized and shaped for snug seating in said channels spanning and stretching the disc tissue to maintain a desired disc space between the adjoining vertebrae bodies with opposite faces bottomed on at least the cortex bone portion of both adjacent bodies, said plug having at least one open ended slot therethrough exposed to the bone and adapted to be packed with bone implant material, and irregular surfaces on said plug having passages therebetween communicating with said slot and facilitating ingrowth of bone implant material from the slot and bone from the vertebrae bodies bottomed thereon to fuse said bodies together in fixed relation.

2. A prosthetic device adapted for fusing together adjoining vertebrae with spaced opposed faces on opposite sides of a damaged collapsed vertebrae disc having tissue connecting the adjoining vertebrae bodies, said opposed faces of the vertebrae bodies having a pair of laterally spaced posterior to anterior extending transverse channels cut therein, and said disc tissue having openings therethrough aligned with the channels, which comprises a rigid inert plug having a greater height than the damaged disc space between the bottoms of the aligned channels for force fit into the channels to stretch the disc tissue to maintain the original undamaged disc space, and spaced nubs radiating from said plug for biting into surfaces of the channels and having passages therebetween to facilitate ingrowth of bone from the vertebrae bodies bottomed in the channels to fuse the bodies together in fixed relation.

3. A surgical prosthetic device adapted for fusing together adjoining vertebrae bodies which comprises a parallelepiped inert rigid plug having top, bottom, and side walls, a leading end and a trailing end, said leading end having a reduced nose surrounded by bevelled edges diverging to said top, bottom and side walls in spaced relation from each other, each nub having an inclined front face and a back wall cooperating therewith to define a sharp biting edge at the intersection thereof, and an open end slot through said plug between said leading and trailing ends communicating with said nubs and adapted to be packed with bone implant material.

4. The device of claim 3 including a first slot open to the top and bottom walls of the plug and a second slot intersecting the first slot open to the side walls of the plug.

5. The device of claim 3, wherein the plug has a length greater than height and a width less than height.

6. The device of claim 3, wherein the plug is composed of radiolucent material.

7. The device of claim 1, wherein the channels have flat sides and extend in a posterior to anterior direction.

8. The device of claim 1, wherein the plug has two slots intersecting each other at the longitudinal axis of the plug.

9. The device of claim 1, wherein the nubs have front faces sloping in the direction of insertion into the channels and sharp edges at their apices.

10. The device of claim 2, wherein the plug is a parallelepiped.

11. The device of claim 2, wherein the plug is composed of radiolucent material.

* * * * *

UNITED STATES PATENT AND TRADEMARK OFFICE
CERTIFICATE OF CORRECTION

PATENT NO. : 4,834,757
DATED : May 30, 1989
INVENTOR(S) : John W. Brantigan

It is certified that error appears in the above—identified patent and that said Letters Patent is hereby corrected as shown below:

Column 1, line 37, after "4,743,256", insert --and--;

Column 5, line 54, after "19c" delete "a";

Column 7, line 3, delete "longitudinally" and insert --longitudinaly--

Claim 3, column 8, line 23, after "side walls" insert --, said trailing end having a longitudinal tool receiving recess, nubs radiating from said top, bottom and side walls--.

Signed and Sealed this

Twenty-second Day of May, 1990

Attest:

HARRY F. MANBECK, JR.

*Attesting Officer* — *Commissioner of Patents and Trademarks*